US005262434A

United States Patent [19]

Jautelat et al.

[11] Patent Number: 5,262,434

[45] Date of Patent: Nov. 16, 1993

[54] HALOGENOALKYL-AZOLYL DERIVATIVES

[75] Inventors: Manfred Jautelat, Burscheid; Jürgen Scherkenbeck, Leverkusen; Klaus Stroech, Solingen; Stefan Dutzmann, Hilden; Heinz Dehne, Monheim; Gerd Haenssler, Leverkusen; Karl-Heinz Kuck, Langenfeld, all of Fed. Rep. of Germany

[73] Assignee: Bayer Aktiengesellschaft, Leverkusen, Fed. Rep. of Germany

[21] Appl. No.: 929,849

[22] Filed: Aug. 14, 1992

Related U.S. Application Data

[63] Continuation of Ser. No. 737,639, Jul. 30, 1991, abandoned.

[30] Foreign Application Priority Data

Aug. 9, 1990 [DE] Fed. Rep. of Germany ....... 4025204
Jan. 10, 1991 [DE] Fed. Rep. of Germany ....... 4100516

[51] Int. Cl.$^5$ .................. A01N 43/653; C07D 249/08

[52] U.S. Cl. .................................... 514/383; 514/184; 548/101; 548/267.8; 548/268.6

[58] Field of Search ............................... 514/184, 383; 548/267.8, 268.6, 101

[56] References Cited

U.S. PATENT DOCUMENTS 4,616,027 10/1986 Richardson et al. ............ 548/267.8
4,715,887 12/1987 Kramer et al. ......................... 71/92
4,935,436 6/1990 Markley et al. .................. 548/267.8

FOREIGN PATENT DOCUMENTS 0097425 1/1984 European Pat. Off. .
0380277 8/1990 European Pat. Off. .
9008140 7/1990 PCT Int'l Appl. .

*Primary Examiner*—Patricia L. Morris
*Attorney, Agent, or Firm*—Sprung Horn Kramer & Woods

[57] ABSTRACT

New halogenoalkyl-azolyl derivatives of the formula

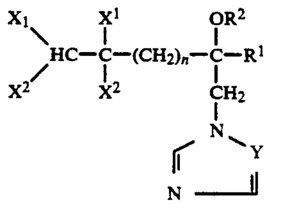

(I)

in which $R^1$ represents optionally substituted phenyl,
$R^2$ represents hydrogen, alkyl, alkenyl, acyl or aralkyl,
$X^1$ represents halogen,
$X^2$ represents halogen,
n represents 0 or 1 and
Y represents nitrogen or a CH group and their acid addition salts and metal salt complexes, are outstandingly effective as microbicides in plant protection and in the preservation of materials.

11 Claims, No Drawings

HALOGENOALKYL-AZOLYL DERIVATIVES

This is a continuation of application Ser. No. 737,639, filed Jul. 30, 1991, now abandoned.

The present invention relates to new halogenoalkyl-azolyl derivatives, to a plurality of processes for their preparation, and to their use as microbicides in plant protection and in the protection of materials.

It has been disclosed that certain dihalogeno-allyl-triazolyl derivatives have fungicidal properties (cf. EP-OS (European Published Specification) 0,097,425). For example, 4-(2,4-dichloro-phenyl)-1,2-dibromo-4-hydroxy-5-(1,2,4-triazol-1-yl)-pent-1-ene and 4-(2,4-dichloro-phenyl)-1,2-dichloro-4-hydroxy-5-(1,2,4-triazol-1-yl)-pent-1-ene can be employed for combating fungi. The action of these substances is good, but leaves something to be desired in some cases when low application rates are employed.

Furthermore, it has already been disclosed that certain halogenoalkyl-triazolyl derivatives which contain an optionally substituted phenyl radical on the central carbon atom are suitable as fungicides against phytopathogenic fungi (cf. EP-OS (European Published Specification) 0,380,277). However, corresponding compounds which contain a halogenoalkyl radical which has been dihalogenated in the position adjacent to the central carbon atom are not described. Substances of this type which have, on the central carbon atom, an n-propyl radical which is in each case dihalogenated in the 2- and 3-position, are furthermore also not disclosed.

New halogenoalkyl-azolyl derivatives of the formula

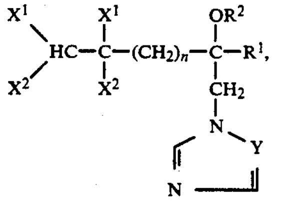

(I)

in which $R^1$ represents optionally substituted phenyl, $R^2$ represents hydrogen, alkyl, alkenyl, acyl or aralkyl, $X^1$ represents halogen, $X^2$ represents halogen, n represents 0 or 1 and Y represents nitrogen or a CH group, and their acid addition salts and metal salt complexes have now been found.

The compounds of the formula (I) contain at least one asymmetrically substituted carbon atom and can therefore be obtained in the forms of optical isomers. The present invention relates to the mixtures of isomers as well as to the individual isomers.

Furthermore, it has been found that halogenoalkyl-azolyl derivatives of the formula (I) and their acid addition salts and metal salt complexes are obtained when alkines of the formula

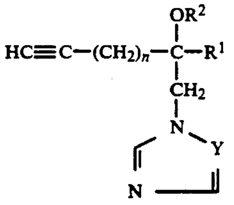

(II)

in which $R^1$, $R^2$, Y and n have the abovementioned meanings are reacted with halogen or halogen-donating compounds in the presence of a diluent, and, if desired, the resulting compounds of the formula (I) are subsequently subjected to an addition reaction with an acid or a metal salt.

Finally, it has been found that the new halogenoalkyl-azolyl derivatives of the formula (I) and their acid addition salts and metal salt complexes have powerful microbicidal properties and can be employed in plant protection as well as in the protection of materials.

Surprisingly, the substances according to the invention have a better microbicidal activity in plant protection as well as in the protection of materials than those previously known compounds of the same direction of action which have the most similar constitution.

In the compounds of the formulae (I) and (II), $R^1$ preferably represents phenyl which can be monosubstituted to trisubstituted by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms phenyl which is optionally monosubstituted or disubstituted by identical or different halogen substituents, phenoxy which is optionally monosubstituted or disubstituted by identical or different halogen substituents, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano.

$R^2$ preferably represents hydrogen, alkyl having 1 to 6 carbon atoms, alkenyl having 3 to 6 carbon atoms, acyl having 1 to 4 carbon atoms or phenylalkyl having 1 to 4 carbon atoms in the alkyl moiety.

$X^1$ preferably represents fluorine, chlorine or bromine.

$X^2$ preferably represents fluorine, chlorine or bromine.

Particularly preferably, $R^1$ represents phenyl which can be monosubstituted to trisubstituted by identical or different substituents from the series comprising fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, phenyl, chlorophenyl, dichlorophenyl, phenoxy, chlorophenoxy, dichlorophenoxy, methoxycarbonyl, ethoxycarbonyl, methoximinomethyl, 1-methoximinoethyl, nitro and/or cyano.

$R^2$ particularly preferably represents hydrogen, methyl, ethyl, n-propyl, isopropyl, n-butyl, allyl, formyl, acetyl, benzyl or phenethyl.

$X^1$ particularly preferably represents fluorine, chlorine or bromine.

$X^2$ particularly preferably represents fluorine, chlorine or bromine.

The index n represents 0 or 1.

Y represents nitrogen or a CH group.

Other preferred substances according to the invention are addition products of acids and halogenoalkyl-azolyl derivatives of the formula (I) in which $R^1$, $R^2$, $X^1$, $X^2$, Y and n have the meanings which have already been mentioned as being preferred or particularly preferred for these radicals and the index n.

The acids which can be added on preferably include hydrohalic acids such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids such as, for example, p-toluenesulophonic acid, 1,5-naphthalenedisulphonic acid, camphorsulphonic acid or saccharin.

Other preferred compounds according to the invention are addition products of salts of metals of main groups II to IV and of subgroups I and II and IV to VIII of the periodic system of the elements and of halogenoalkylazolyl derivatives of the formula (I) in which $R^1$, $R^2$, $X^1$, $X^2$, Y and n have the meanings which have already been mentioned as being preferred or particularly preferred for these radicals and the index n. In this context, salts of copper, zinc, manganese,, magnesium, tin, iron and of nickel are particularly preferred. Suitable anions of these salts are those which are derived from those acids which lead to physiologically acceptable addition products. In this connection, particularly preferred acids of this type are the hydrohalic acids such as, for example, hydrochloric acid and hydrobromic acid, furthermore phosphoric acid, nitric acid and sulphuric acid.

Examples of substances according to the invention which may be mentioned are the halogenoalkyl-azolyl derivatives listed in the table below.

TABLE 1

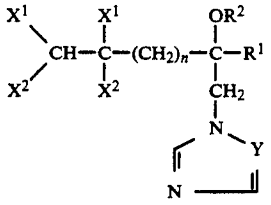

| $X^1$ | $X^2$ | n | $R^1$ | $R^2$ | Y |
|---|---|---|---|---|---|
| Cl | Cl | 0 | 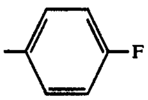 | H | N |
| Cl | Cl | 1 | 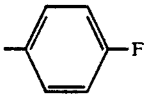 | H | N |

TABLE 1-continued

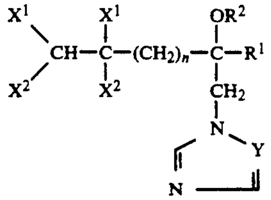

| $X^1$ | $X^2$ | n | $R^1$ | $R^2$ | Y |
|---|---|---|---|---|---|
| Cl | Cl | 1 | 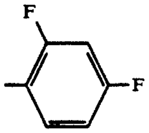 | H | N |
| Cl | Br | 1 | 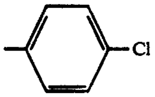 | H | N |
| Cl | Cl | 0 | 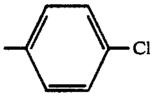 | H | CH |
| Cl | Cl | 0 | 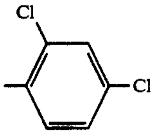 | H | N |
| Cl | Cl | 0 | 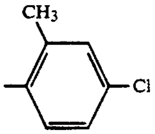 | H | N |
| Cl | Cl | 0 | 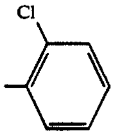 | H | N |
| Cl | Cl | 0 | 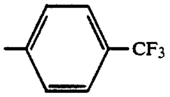 | H | N |
| Cl | Cl | 1 | 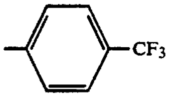 | H | N |
| Cl | Cl | 0 | 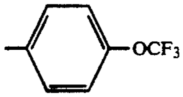 | H | N |
| Cl | Cl | 1 | 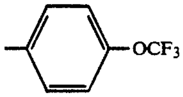 | H | N |
| Cl | Cl | 0 | 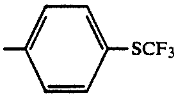 | H | N |

TABLE 1-continued

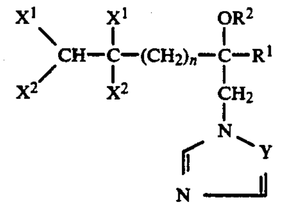

| $X^1$ | $X^2$ | n | $R^1$ | $R^2$ | Y |
|---|---|---|---|---|---|
| Cl | Cl | 1 | 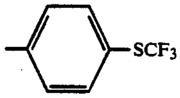 | H | N |

If 3-(4-chlorophenyl)-3-hydroxy-4-(1,2,4-triazol-1-yl)-but-1-ine is used as starting substance and chlorine gas as reactant, the course of process (a) according to the invention can be illustrated by the following equation:

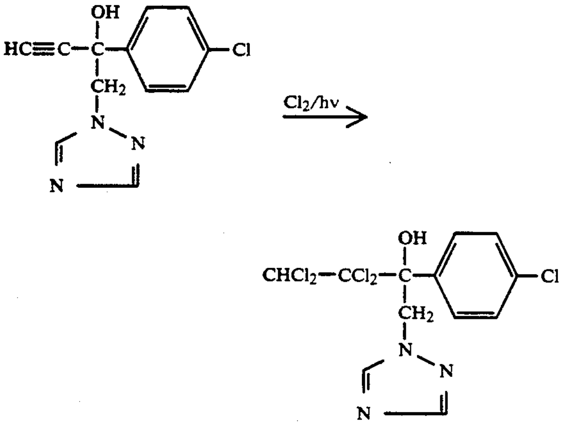

The alkines of the formula (II) which are required as starting substances for carrying out the process according to the invention are known in some cases (cf. EP-OS (European Published Specification) 0,096,786 and EP-OS (European Published Specification) 0,353,558). They can be prepared by reacting a) azolyl-methyl ketones of the formula

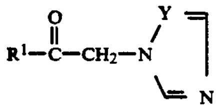 (III)

in which $R^1$ and Y have the abovementioned meanings, either

α) with acetylene salts of the formula $HC \equiv CMe$ (IV)

in which Me represents an equivalent of a metal cation, in the presence of a diluent, or β) with propargyl halides of the formula $HC \equiv C—CH_2—Hal$ (V)

in which Hal represents chlorine or bromine, in the presence of activated aluminium and in the presence of a diluent, and, if desired, reacting the resulting alkines of the formula

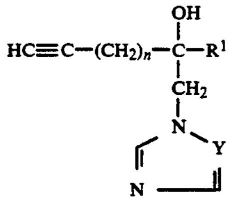 (IIa)

in which $R^1$, Y and n have the abovementioned meanings, with strong bases in the presence of a diluent, and reacting the resulting alcoholates of the formula

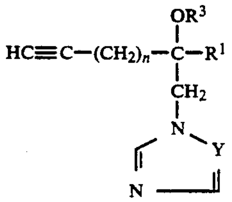 (IIb)

in which $R^1$, Y and n have the abovementioned meanings and $R^3$ represents a cationic radical of a base, with halogen compounds of the formula $R^4—Hal'$ (VI)

in which $R^4$ represents alkyl, alkenyl, acyl or aralkyl and

Hal' represents chlorine, bromine or iodine, in the presence of a diluent, or reacting b) chloromethyl ketones of the formula

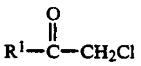 (VII)

in which $R^1$ has the abovementioned meaning, either

α) with acetylenes of the formula $HC \equiv CR^5$ (VIII)

in which $R^5$ represents hydrogen or an equivalent of a metal cation, if appropriate in the presence of a base and in the presence of a diluent, or β) with propargyl halides of the formula $HC \equiv C—CH_2—Hal$ (V)

in which Hal has the abovementioned meaning, under the conditions of process (a), variant β, and then reacting the resulting hydroxyalkines of the formula

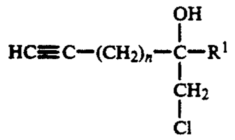
(IX)

in which $R^1$ and n have the abovementioned meanings, with azoles of the formula

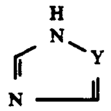
(X)

in which Y has the abovementioned meaning, in the presence of an acid-binding agent and in the presence of a diluent and, if desired, further reacting the resulting alkines of the formula

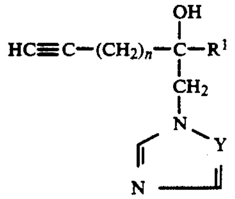
(IIa)

in which $R^1$, Y and n have the abovementioned meanings, in accordance with process (a).

The azolyl-methyl ketones of the formula (III) required as starting substances for carrying out process (a) are known or can be prepared in a simple manner by the processes known in principle (cf. DE-OS (German Published Specification) 2,431,407 and EP-OS (European Published Specification) 0,353,558).

Formula (IV) provides a general definition of the acetylene salts required as reactants when carrying out process (a), variant α. In this formula, Me preferably represents a lithium cation or an equivalent of a cerium-(III) cation.

The acetylene salts of the formula (IV) are known (cf. Houben-Weyl, "Methoden der Organischen Chemie [Methods in Organic Chemistry]", Vol. V/2a, pages 509 et seq., Georg Thieme Verlag, Stuttgart 1977 and Tetrahedron Letters 25, (1984) 4233).

Diluents which can be used for carrying out the first step of process (a), variant α, are all inert organic solvents which are customary for reactions of this type. Ethers such as tetrahydrofuran or diethyl ether, and also hydrocarbons such as n-hexane, are preferably suitable.

When carrying out the first step of process (a), variant α, the reaction temperatures can be varied within a substantial range. In general, the variant is carried out at temperatures between −78° C. and +30° C., preferably at temperatures between −70° C. and +20° C.

Process (a) as well as the process according to the invention and process (b) are generally carried out under atmospheric pressure.

When carrying out the first step of process (a), variant α, a procedure is generally followed in which the acetylene salts are prepared first, and these are then reacted, with an equivalent amount or an excess or a deficiency, of azolyl-methyl ketone of the formula (III) without having been isolated previously. Working-up is carried out by customary methods. In general, a procedure is followed in which the reaction mixture is first treated with an aqueous salt solution, for example ammonium chloride solution, the mixture is then extracted by shaking several times with an organic solvent which is sparingly soluble in water, and the combined organic phases are dried and then concentrated under reduced pressure.

The propargyl halides of the formula (V) which are required as reactants for carrying out process (a), variant β, are known.

Diluents which can be used for carrying out the first step of process (a), variant β, are all inert organic solvents which are customary for reactions of this type. Ethers such as tetrahydrofuran or diethyl ether are preferably suitable.

The first step of process (a), variant β, is carried out in the presence of activated aluminium. The latter is prepared by adding catalytic amounts of mercury(II) chloride and iodine to aluminium flakes.

When carrying out the first step of process (a), variant β, the reaction temperatures can be varied within a substantial range. In general, the variant is carried out at temperatures between −80° C. and +100° C., preferably at temperatures between −70° C. and +60° C.

When carrying out the first step of process (a), variant β, a procedure is generally followed in which 1 to 2 mol of propargyl halide of the formula (V) and 1 to 1.5 mol of aluminium and catalytic amounts of mercury(II) chloride and iodine are employed per mole of azolylmethyl ketone of the formula (III). The resulting products are isolated by customary methods.

When carrying out the second step of process (a), the alkines of the formula (IIa) are converted into the corresponding alcoholates by reacting them with suitable strong bases such as alkali metal amides or alkali metal hydrides, quaternary ammonium hydroxides or phosphonium hydroxides in an inert diluent such as, for example, dioxane, at room temperature. Accordingly, $R^3$ in the compounds of the formula (IIb) preferably represents an alkali metal cation such as a sodium or potassium cation, or a quaternary ammonium or phosphonium cation.

Formula (VI) provides a general definition of the halogen compounds required as reactants for carrying out the third step of process (a). In this formula, $R^4$ preferably represents those meanings which have already been mentioned for the substituent $R^2$ in connection with the description of the substances of the formula (I) according to the invention, with the exception of the meaning of hydrogen. Hal' represents chlorine, bromine or iodine.

The halogen compounds of the formula (VI) are known or can be prepared by methods known in principle.

Suitable diluents for carrying out the second and third steps of process (a) are inert organic solvents. The following can preferably be used: ethers such as diethyl ether or dioxane; aromatic hydrocarbons such as benzene; and in individual cases also chlorinated hydrocarbons such as chloroform, methylene chloride or carbon tetrachloride; as well as hexamethylphosphoric triamide.

When carrying out the second and third steps of process (a), the reaction temperatures can be varied within a substantial range. In general, the steps are carried out at temperatures between 0° C. and 120° C., preferably between 20° C. and 100° C.

When carrying out the second step of process (a), alkines of the formula (IIa) are first reacted with strong bases to give the corresponding alcoholates of the formula (IIb). In the third step which follows, 1 to 2 mol of halogen compound of the formula (VI) are preferably employed per mole of an alcoholate of the formula (IIb). To isolate the end product, the reaction mixture is freed from the solvent, and the residue is treated with water and an organic solvent. The organic phase is separated off, and is worked up and purified in a customary manner.

In a preferred embodiment, a procedure is expediently followed in the second and third steps of process (a) in which, starting with a hydroxy compound of the formula (IIa), the latter is converted, in a suitable organic solvent, by means of alkali metal hydride or alkali metal amide into the alkali metal alcoholate, and the latter is immediately reacted with a halogen compound of the formula (VI), without isolation, during which process the compounds of the formula (II) are obtained in one operation, with alkali metal halide being separated out.

According to a further preferred embodiment, the preparation of the alcoholates and the reaction with a halogen compound of the formula (VI) are expediently carried out in a two-phase system such as, for example, aqueous sodium or potassium hydroxide solution/toluene or methylene chloride, with the addition of 0.01 bis 1 mol of a phase-transfer catalyst such as, for example, ammonium or phosphonium compounds, the reaction of the alcoholates with the halides which are in the organic phase taking place in the organic phase or at the interface.

Formula (VII) provides a general definition of the chloromethyl ketones required as starting substances for carrying out process (b). In this formula, $R^1$ preferably has those meanings which have already been mentioned in connection with the description of the substances of the formula (I) according to the invention as being preferred for this radical.

The chloromethyl ketones of the formula (VII) are known or can be prepared by methods known in principle (cf. DE-OS (German Published Specification) 3,049,461).

Formula (VIII) provides a general definition of the acetylenes required as reactants in process (b), variant $\alpha$. In this formula, $R^5$ preferably represents hydrogen, a lithium cation or an equivalent of a magnesium or cerium(III) cation.

The acetylenes of the formula (VIII) are known.

Suitable bases for carrying out the first step of process (b), variant $\alpha$, are all strong bases which are customary for reactions of this type. Alkali metal hydroxides such as potassium hydroxide can preferably be used.

Diluents for carrying out the first step of process (b), variant $\alpha$, are all inert organic solvents which are customary for reactions of this type. Ethers such as tetrahydrofuran or diethyl ether are preferably suitable.

When carrying out the first step of process (b), variant $\alpha$, the reaction temperatures can be varied within a substantial range. In general, the variant is carried out at temperatures between $-78°$ C. and $+50°$ C., preferably between $-78°$ C. and $+40°$ C.

When carrying out the first step of process (b), variant $\alpha$, a procedure is generally followed in which chloromethyl ketones of the formula (VII) and acetylenes of the formula (VIII) are reacted in approximately equivalent amounts. However, it is also possible to use one or other component in excess. Working-up is carried out by customary methods.

The first step of process (b), variant $\beta$, is carried out under those conditions which are also employed in the first step of process (a), variant $\beta$.

The hydroxyalkines of the formula (IX) can be further reacted directly with azoles of the formula (X). Alternatively, they can first be converted into oxiranes and these are then reacted with azoles of the formula (X).

Suitable acid-binding agents for carrying out the second step of process (b) are all customary acid acceptors. The following can preferably be used: alkali metal carbonates and hydrogen carbonates such as sodium carbonate, potassium carbonate or sodium hydrogen carbonate, furthermore tertiary aliphatic or aromatic amines such as triethylamine, N,N-dimethyl-cyclohexyl-amine, N,N-dimethyl-benzyl-amine and pyridine, and also cyclic amines such as 1,5-diaza-bicyclo[4.3.0]-non-5-ene (DEN), 1,8-diaza-bicyclo[5.4.0]undec-7-ene (DBU) and 1,4-diaza-bicyclo[2.2.2]octane (DABCO).

Suitable diluents for carrying out the second step of process (b) are all inert organic solvents. The following can preferably be used: aliphatic and aromatic, optionally halogenated hydrocarbons such as pentane, hexane, cycloliexane, petroleum ether, benzine, ligroin, benzene, toluene, xylene, methylene chloride, ethylene chloride, chloroform,, carbon tetrachloride, chlorobenzene and o-dichlorobenzene, ethers such as diethyl ether and dibutyl ether, and also tert.-butyl methyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, and pyridine.

When carrying out the second step of process (b), the reaction temperatures can also be varied within a substantial range. In general, this step is carried out at temperatures between 0° C. and 200° C., preferably between 20° C. and 150° C.

When carrying out the second step of process (b), a procedure is generally followed in which an equivalent amount or even an excess of azole of the formula (X) and 2 to 3 mol of acid-binding agent are employed per mole of hydroxyalkine of the formula (IX). Working-up is carried out by customary methods. The further reaction of the alkines of the formula (IIa), which may be desired, is carried out in process (b) in the same manner as in process (a).

Suitable halogens as reactants for carrying out the process according to the invention are preferably fluorine, chlorine and bromine, furthermore mixed halogens such as chlorine monofluoride, bromine monofluoride or bromine monochloride (see Methodicum Chimicum, F. Korte, Vol. 7, p. 842 (1976)).

Halogen-donating compounds which can be used are, for example, sulphuryl chloride, N-bromosuccinimide with hydrochloric acid, N-chlorosuccinimide with hydrobromic acid or N-chlorosuccinimide with hydrogen fluoride/pyridine (see Synthesis 1973, 780).

The addition reaction of the halogens with the alkines of the formula (II) can be favoured by the action of light, by heat, by free-radical-forming substances such as organic peroxides, by surface-active substances such as active carbon, or metal salts, such as copper(II) chloride or iron(III) chloride.

Diluents which can be employed for carrying out the process according to the invention are all inert organic solvents which are customary for reactions of this type. Halogenated aliphatic hydrocarbons such as methylene chloride, chloroform and carbon tetrachloride can preferably be used.

When carrying out the process according to the invention, the temperatures can be varied within a certain range. In general, the process is carried out at temperatures between −10° C. and +120° C., preferably between −5° C. and +80° C.

When carrying out the process according to the invention, an equivalent amount or an excess of halogen, or halogen-donating compound, is generally employed per mole of alkine of the formula (II). If it is intended to prepare halogenoalkyl-azolyl derivatives of the formula (I) in which $X^1$ differs from $X^2$, a procedure is expediently followed in which the alkine of the formula (II) is first subjected to an addition reaction with 1 mol of a certain halogen, and then, in a second step, this product is subjected to an addition reaction with 1 mol of another halogen. Working-up is carried out by customary methods. In general, a procedure is followed in which the mixture is diluted with an organic solvent which is sparingly soluble in water, washed with water, and the organic phase is dried and then concentrated. However, it is also possible, once the reaction has ended, to concentrate the reaction mixture directly by stripping off the volatile components under reduced pressure. If desired, the products which are formed can be further purified by customary methods.

The halogenoalkyl-azolyl derivatives of the formula (I) which can be obtained by the process according to the invention can be converted into acid addition salts or metal salt complexes.

Preferred acids for the preparation of acid addition salts of compounds of the formula (I) are those which have already been mentioned in connection with the description of the acid addition salts according to the invention as being preferred acids.

The acid addition salts of the compounds of the formula (I). can be obtained in a simple manner by customary salt formation methods, for example by dissolving a compound of the formula (I) in a suitable inert solvent and adding the acid, for example hydrochloric acid, and they can be isolated in a known manner, for example by filtration, and, if desired, purified by washing with an inert organic solvent.

Preferred salts of metals for the preparation of metal salt complexes of the compounds of the formula (I) are those which have already been mentioned in connection with the description of the metal salt complexes according to the invention as being preferred metal salts.

The metal salt complexes of the compounds of the formula (I) can be obtained in a simple manner by customary processes, for example by dissolving the metal salt in alcohol, for example ethanol, and adding the solution to compounds of the formula (I). Metal salt complexes can be isolated in a known manner, for example by filtration, and, if desired, purified by recrystallisation.

The active compounds according to the invention have a powerful microbicidal activity and can be employed in plant protection and in the protection of materials for combating undesired microorganisms such as fungi and bacteria.

Fungicides in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubensis;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminea;*
(conidia form: Drechslera, syn: Helminthosporium);
Cochliobolus species, such as *Cochliobolus sativus;*
(conidia form: Drechslera, syn: Helminthosporium);
Uromyces species, such as *Uromyces appendiculatus;*
Puccinis species, such as *Puccinia recondita;*
Tilletia species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae* and
Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating diseases of cereals and rice, such as Pseudocercosporella, Erysiphe, Fusarium, Pyrenophora, Cochliobolilus, Septoria, Pyricularia and Pellicularia, and for combating powdery mildew of cucumbers and apple scab, and moreover for combating Botrytis in fruit growing, viticulture and vegetable growing. Moreover, they have a good and broad in-vitro action and are suitable for combating powdery mildews, such as *Rhizoctonia solani.*

In the protection of materials, the substances according to the invention can be employed for protecting industrial materials against infestation with, and destruction by, undesired microorganisms.

Industrial materials in the present context are understood as meaning non-living materials which have been prepared for use in industry. For example, industrial materials which are intended to be protected by active compounds according to the invention from microbial change or destruction can be glues, sizes, paper and board, textiles, leather, wood, paints and plastic articles, cooling lubricants and other materials which can be infested with, or destroyed by, microorganisms. Parts of production plants, for example cooling-water circuits, which may be impaired by the multiplication of microorganisms may also be mentioned within the scope of the materials to be protected. Industrial materials which may be mentioned within the scope of the present invention are preferably glues, sizes, papers and boards, leather, wood, paints, cooling lubricants and heat-transfer liquids, particularly preferably wood.

Microorganisms, capable of bringing about degradation of, or change in, the industrial materials, which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa* and
Staphylococcus, such as *Staphylococcus aureus.*

Depending on their particular physical and/or chemical properties, the active compounds can be converted into customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanal or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose, natural and synthetic polymers in the form of powders, granules or latices, such as gum arabic, polyvinyl alcohol, polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

In plant protection, the formulations in general contain between 0.1 and 95 per cent by weight of active compound, preferably between 0.5 and 90%.

When used in plant protection,, the active compounds according to the invention can be present in the formulations as a mixture with other known active compounds, such as fungicides, insecticides, acaricides and herbicides, and in mixtures with fertilizers and growth regulators.

When used in plant protection, the active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

In the treatment of the soil, active compound concentrations of 0.00001 to 0.1% by weight, preferably 0.0001 to 0.02%, are required at the place of action.

The microbicidal agents used for the protection of industrial materials contain the active compounds, in general, in an amount of from 1 to 95% by weight, preferably from 10 to 75% by weight.

When used in the protection of materials, the use concentrations of active compounds according to the invention depend on the nature and the occurrence of the microorganisms to be combated and on the composition of the material to be protected. The optimum dosage rate can be determined by serial tests. In general, the use concentrations are in the range from 0.001 to 5% by weight, preferably from 0.05 to 1.0% by weight, relative to the material to be protected.

When used in the protection of materials, the active compounds according to the invention can also be used as a mixture with other known active compounds.

Examples of active compounds which may be mentioned are the following: Benzyl alcohol mono(poly)-hemiformal and other formaldehyde-releasing compounds, benzimidazolyl-methyl carbamates, tetramethylthiuram disulphide, zinc salts of dialkyldithiocarbamates, 2,4,5,6-tetrachloroisophthalonitrile, thiazolylbenzimidazole, mercaptobenzothiazole, 2-thiocyanatomethylthiobenzothiazole, methylene bisthiocyanate, and phenol derivatives such as 2-phenylphenol, (2,2'-dihydroxy-5,5'-dichloro)-diphenylmethane and 3-methyl-4-chloro-phenol, organotin compounds, tri-halogenomethylthio compounds such as folpet, fluorfolpet and dichlofluanid.

The following examples illustrate the preparation and the use of the active compounds according to the invention.

PREPARATION EXAMPLES

Example 1

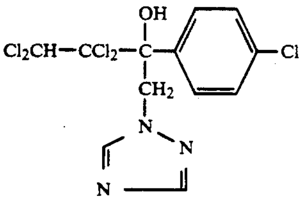

(I-1)

2.5 g (10 mmol) of 3-(4-chlorophenyl)-3-hydroxy-4-(1,2,4-triazol-1-yl)-but-1-ine are chlorinated in 50 ml of methylene chloride at 10° C. in the course of 30 hours under illumination with a 300 watt UV lamp, by passing in chlorine gas. For working up, the resulting suspension is diluted with methylene chloride and extracted by shaking with an aqueous sodium carbonate solution. The organic phase is dried over sodium sulphate and then evaporated under reduced pressure. In this manner, 3.8 g (97% of theory) of 3-(4-chlorophenyl)-3-hydroxy-4-(1,2,4-triazol-1-yl)-1,1,2,2-tetrachlorobutane are obtained in the form of a solid substance of melting point 168° to 169° C.

$^1$H NMR (200 MHz; DMSO): δ=5.05 and 5.45 (AB system; 2H), 6.4 (s; 1H) 7.1 (OH), 7.35 and 7.7 (4H), 7.75 (s; 1H), 8.35 (s; 1H).

Preparation of the starting substance

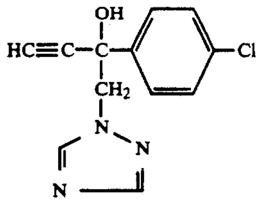

(II-1)

5.0 g (23.2 mmol) of 4-chloro-3-(4-chlorophenyl)-3-hydroxy-1-butine in 50 ml of absolute acetonitrile are refluxed for 5.5 hours together with 1.6 g (23.3 mmol) of 1,2,4-triazole and 6.4 g (46.4 mmol) of anhydrous potassium carbonate. The mixture is then diluted with dichloromethane and extracted several times by shaking with water. After the organic phase has been dried and evaporated, 5.8 g of crude product are obtained which crystallises after filtration with ethyl acetate over 100 g of silica gel and re-concentration. In this manner, 3-(4-chlorophenyl)-3-hydroxy-4-(1,2,4-triazolyl-1)-1-butine is obtained in the form of a solid substance of melting point 90°-94° C.

$^1$H NMR ($CDCl_3$): δ2.65 (s,1H), 4.4 (AB, 2H), 5.8 (OH), 7.35 and 7.45 (4H), 7.85 (s,1H), 8.15 (s, 1H).

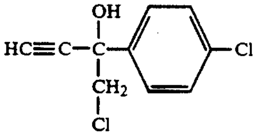

(IX-1)

80 ml (0.2 mol) of a 23% strength solution of butyllithium in hexane are added dropwise at −70° C. to the solution of 5.2 g (0.2 mol) of acetylene in 200 ml of absolute tetrahydrofuran. After 10 minutes, the solution of 28.35 g (0.15 mol) of 4,ω-dichloroacetophenone in 100 ml of absolute tetrahydrofuran is introduced. Stirring is continued for 2 hours at −70° C., and the reaction is stopped by dropwise addition of the mixture of 20 ml of methanol and 20 ml of acetic acid. The solvent is stripped off in vacuo and the remaining mixture is dissolved in dichloromethane and then extracted several times by shaking using saturated aqueous ammonium chloride solution. After the organic phase has been dried and distilled off, 27.8 g of crude product with a content of 76.3% of 4-chloro-3-(4-chlorophenyl)-3-hydroxy-1-butine and 17.6% of starting material, which is filtered off with suction after crystallisation, are obtained.

$^1$H NMR ($CDCl_3$): δ=2.8 (s,1H), 3.4 (OH), 3.75 (AB, 2H) 7.4 and 7.65 (4H).

The substances which are listed in the table below by way of their formulae are also prepared by the method described in Example 1:

TABLE 2

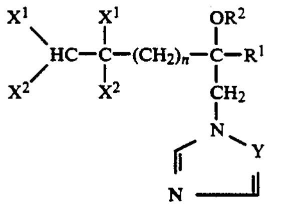

(I)

| Example No. | Compound No. | $X^1$ | $X^2$ | n | $R^1$ | $R^2$ | Y | Physical constants |
|---|---|---|---|---|---|---|---|---|
| 2 | I-2 | Cl | Cl | 1 | 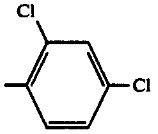 | H | N | GC/MS(Cl): 436(M + $H^+$) |
| 3 | I-3 | Cl | Cl | 1 | 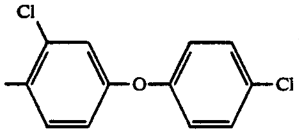 | H | N | melting point 142-144° C. |
| 4 | I-4 | Cl | Cl | 1 | 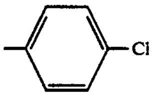 | H | N | NMR(200 MHZ, $CDCl_3$): δ 3.15 (AB, 2H), 4.5(AB, 2H), 7.6(s, 1H), 7.3(4H), 7.9(s, 1H), 8.0(s, 1H) |
| 5 | I-5 | Cl | Cl | 1 | 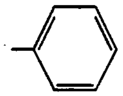 | H | N | GC/MS(Cl): 368(M + $H^+$) |

In the use examples which follow, the compounds of the formulae given below were employed as comparison substances:

(A) = 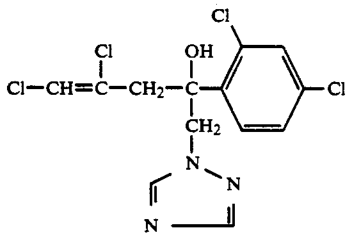

(Disclosed in EP-OS (European Published Specification) 0,097,425).

(B) = 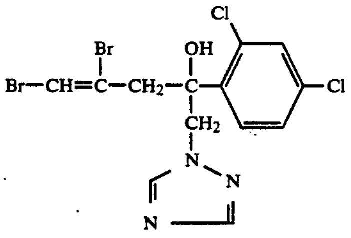

(Disclosed in EP-OS (European Published Specification) 0,097,425).

Example A

Erysiphe test (barley)/protective

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp.hordei.

The plants are placed in a greenhouse at a temperature of about 20° C. and a relative atmospheric humidity of about 80%, in order to promote the development of mildew pustules.

Evaluation is carried out 7 days after the inoculation.

In this test, substances (I-1), (I-2), (I-4) (I-5) according to the invention show a considerably better activity than comparison substances (A) and (B).

Example B

Erysiphe test (wheat)/protective

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp.tritici.

The plants are placed in a greenhouse at a temperature of about 20° C. and a relative atmospheric humidity of about 80%, in order to promote the development of mildew pustules.

Evaluation is carried out 7 days after the inoculation.

In this test, compounds (I-1), (I-2), (I-4) and (I-5) according to the invention shows a considerably better activity than comparison substances (A) and (B).

It will be a understood that the specification and examples are illustrative but not limitative of the present invention and that other embodiments within the spirit and scope of the invention will suggest themselves to those skilled in the art.

What is claimed is:

1. A halogenoalkyl-triazolyl derivative of the formula

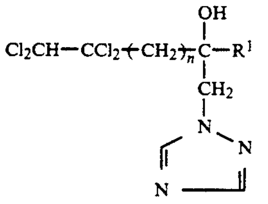

in which $R^1$ represents phenyl which can be monosubstituted or disubstituted by identical or different substituents from the group consisting of chlorine and chlorophenoxy, n represents 0 or 1, or an acid addition salt or metal salt complex thereof.

2. A halogenoalkyl-azolyl derivative or an acid addition salt or metal complex thereof according to claim 1, wherein such compound is 3-4-(chlorophenyl)-3-hydroxy-4-(1,2,4-triazol-1-yl)-1,1,2,2-tetrachlorobutane of the formula

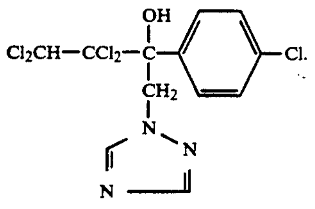

3. A halogenoalkyl-azolyl derivative or an acid addition salt or metal salt complex thereof according to claim 1, wherein such compound is 4-(2,4-dichlorophenyl)-4-hydroxy-5-(1,2,4-triazol-1-yl)-1,1,2,2,-tetrachloropentane of the formula

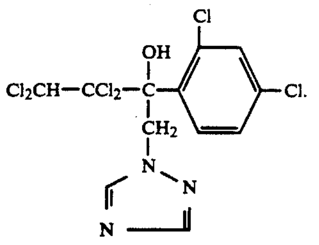

4. A halogenoalkyl-azolyl derivative or an acid addition salt or metal salt complex thereof according to claim 1, wherein such compound is 4-[2-chloro-4-(4-chlorophenyoxy)phenyl]-4-hydroxy-5-(1,2,4-triazol-1-yl)-1,1,2,2-tetrachloropentane of the formula

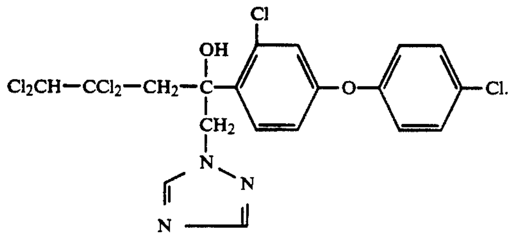

5. A halogenoalky-azolyl derivative or an acid addition salt or metal salt complex thereof according to claim 1, wherein such compound is 4-(4-chlorophenyl)-4-hydroxy-5-(1,2,4-triazol-1-yl)-1,1,2,2-tetrachloro-pentane of the formula

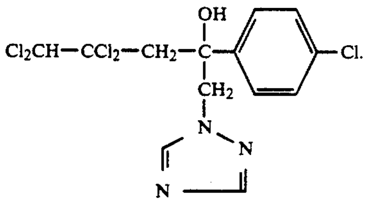

6. A halogenoalkyl-azolyl derivative or an acid addition salt or metal salt complex thereof according to claim 1, wherein such compound is 4-phenyl-4-hydroxy-5-(1,2,4-triazol-1-yl)-1,1,2,2-tetrachloro-pentane of the formula

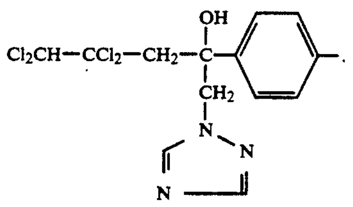

7. A microbicidal composition comprising a microbicidally effective amount of a compound or addition product according to claim 1 and an inert diluent.

8. A fungicidal composition comprising a fungicidally effective amount of a compound or addition product according to claim 1 and an inert diluent.

9. A method of combating undesired microorganisms in plant protection and in the preservation of materials, which method comprises applying to such undesired microorganisms or to their habitat a microbicidally effective amount of a compound or addition product according to claim 1.

10. A method to claim 9, wherein the undesired microorganisms are phytopathogenic fungi.

11. A method according to claim 9, wherein such compound is 3-(4-chlorophenyl)-3-hydroxy-4-(1,2,4-triazol-1-yl)-1,1,2,2-tetrachloro-butane, 4-(2,4-dichlorophenyl)-4-hydroxy-5-(1,2,4-triazol-1-yl)-1,1,2,2-tetrachloro-pentane, 4-[2-chloro-4-(4-chlorophenoxy)-phenyl]-4-hydroxy-5-(1,2,4-triazol-1-yl)-1,1,2,2-tetrachloro-pentane, 4-(4-chlorophenyl)-4-hydroxy-(1,2,4-triaizol-1-yl)-1,1,2,2-tetrachloro-pentane or 4-phenyl-4-hydroxy-5-(1,2,4-triaizol-1-yl)-1,1,2,2-tetrachloro-pentane, or an acid addition salt or metal salt complex thereof.

* * * * *

UNITED STATES PATENT AND TRADEMARK OFFICE

CERTIFICATE OF CORRECTION

PATENT NO. : 5,262,434
DATED : November 16, 1993
INVENTOR(S) : Jautelat, et al.

It is certified that error appears in the above-identified patent and that said Letters Patent is hereby corrected as shown below:

Col. 20, line 5 Delete formula and substitute

-- 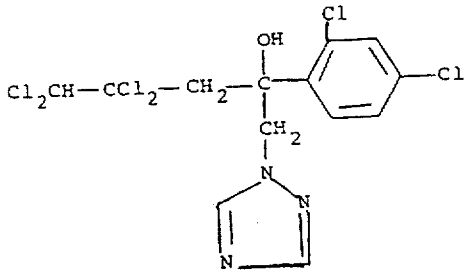 --

Col. 22, line 5 Delete " triaizol " and substitute -- triazol --

Col. 22, line 7 Delete " triaizol " and substitute -- triazol --

Signed and Sealed this

Twenty-seventh Day of July, 1999

Attest:

Q. TODD DICKINSON

Attesting Officer

*Acting Commissioner of Patents and Trademarks*